US009066833B2

(12) United States Patent
Gassner et al.

(10) Patent No.: US 9,066,833 B2
(45) Date of Patent: Jun. 30, 2015

(54) INCONTINENCE ARTICLE IN PANT FORM

(71) Applicant: PAUL HARTMANN AG, Heidenheim (DE)

(72) Inventors: Oliver Gassner, Ulm, DE (US); Andreas Beyrle, Nattheim (DE); Rüdiger Kesselmeier, Herbrechtingen (DE); Krysztof D. Malowaniec, Heidenheim (DE)

(73) Assignee: PAUL HARTMANN AG, Heidenheim (DE)

( * ) Notice: Subject to any disclaimer, the term of this patent is extended or adjusted under 35 U.S.C. 154(b) by 186 days.

(21) Appl. No.: 13/896,609

(22) Filed: May 17, 2013

(65) Prior Publication Data
US 2014/0163509 A1    Jun. 12, 2014

Related U.S. Application Data

(60) Provisional application No. 61/659,449, filed on Jun. 14, 2012.

(30) Foreign Application Priority Data

May 18, 2012 (DE) .......................... 10 2012 208 395

(51) Int. Cl.
*A61F 13/49*    (2006.01)
*A61F 13/53*    (2006.01)
(Continued)

(52) U.S. Cl.
CPC ..... *A61F 13/49019* (2013.01); *A61F 13/49061* (2013.01); *A61F 13/496* (2013.01); *A61F 13/534* (2013.01); *A61F 13/535* (2013.01); *A61F 13/5515* (2013.01);
(Continued)

(58) Field of Classification Search
CPC ................... A61F 13/49058; A61F 13/49061; A61F 13/496; A61F 13/49019; A61F 13/539; A61F 13/55115
See application file for complete search history.

(56) References Cited

U.S. PATENT DOCUMENTS

| 7,211,071 B2 | 5/2007 | Mishima et al. |
| 7,993,320 B2 | 8/2011 | Hornung et al. |

(Continued)

FOREIGN PATENT DOCUMENTS

| DE | 602004011884 | 10/2008 |
| DE | 102007055628 | 5/2009 |

(Continued)

*Primary Examiner* — Susan Su
(74) *Attorney, Agent, or Firm* — Henry M. Feiereisen LLC

(57) ABSTRACT

In an incontinence article in pant form, a crotch section having an absorption body, is connected to stomach and back sections in respective overlapping regions of the crotch section and the stomach section, and the crotch section and the back section, wherein the incontinence article has a first fold axis formed by a transverse center axis of the incontinence article, second fold axes extending outside on either side of the absorption body, and a third fold axis in a region of the absorption body, wherein regions of the stomach section and the back section which laterally protrude over the crotch section are folded about the second fold axes toward the longitudinal center axis, wherein after folding the incontinence article about the third folding axis, the border of the stomach and back band does not protrude over the first fold axis wherein a mass per area of the absorption body decreases from a region of the transverse center axis toward stomach-section side and back-section side ends of the absorption body.

18 Claims, 9 Drawing Sheets

(51) Int. Cl.
*A61F 13/496* (2006.01)
*A61F 13/534* (2006.01)
*A61F 13/535* (2006.01)
*A61F 13/551* (2006.01)
*A61F 13/15* (2006.01)

(52) U.S. Cl.
CPC .............. *A61F 13/15747* (2013.01); *A61F 2013/530437* (2013.01); *A61F 2013/5355* (2013.01)

(56) References Cited

U.S. PATENT DOCUMENTS

| | | |
|---|---|---|
| 2003/0036739 A1 | 2/2003 | Christoffel et al. |
| 2004/0176733 A1* | 9/2004 | Glaug et al. .............. 604/378 |
| 2004/0204698 A1* | 10/2004 | Zenker et al. ............. 604/367 |
| 2005/0027272 A1 | 2/2005 | Suzuki et al. |
| 2006/0178650 A1* | 8/2006 | Hakansson et al. ........ 604/378 |
| 2006/0218700 A1 | 10/2006 | Uda |
| 2007/0208316 A1* | 9/2007 | Nakahata et al. ....... 604/385.02 |
| 2012/0043244 A1 | 2/2012 | Hagner et al. |
| 2012/0043245 A1 | 2/2012 | Hagner et al. |
| 2012/0215191 A1* | 8/2012 | Takino et al. ............. 604/365 |
| 2013/0296819 A1* | 11/2013 | Kikuchi et al. ........... 604/380 |

FOREIGN PATENT DOCUMENTS

| | | |
|---|---|---|
| EP | 0 780 325 | 10/2002 |
| EP | 1 639 908 | 3/2006 |
| EP | 1 140 662 | 5/2006 |
| EP | 1 666 012 | 6/2006 |
| EP | 1 423 069 | 9/2010 |
| JP | 11-113956 | 4/1999 |
| JP | 2000-024029 | 1/2000 |
| WO | WO 2010/101277 | 9/2010 |
| WO | WO 2011/095908 | 8/2011 |
| WO | WO 2013/001825 | 1/2013 |

\* cited by examiner

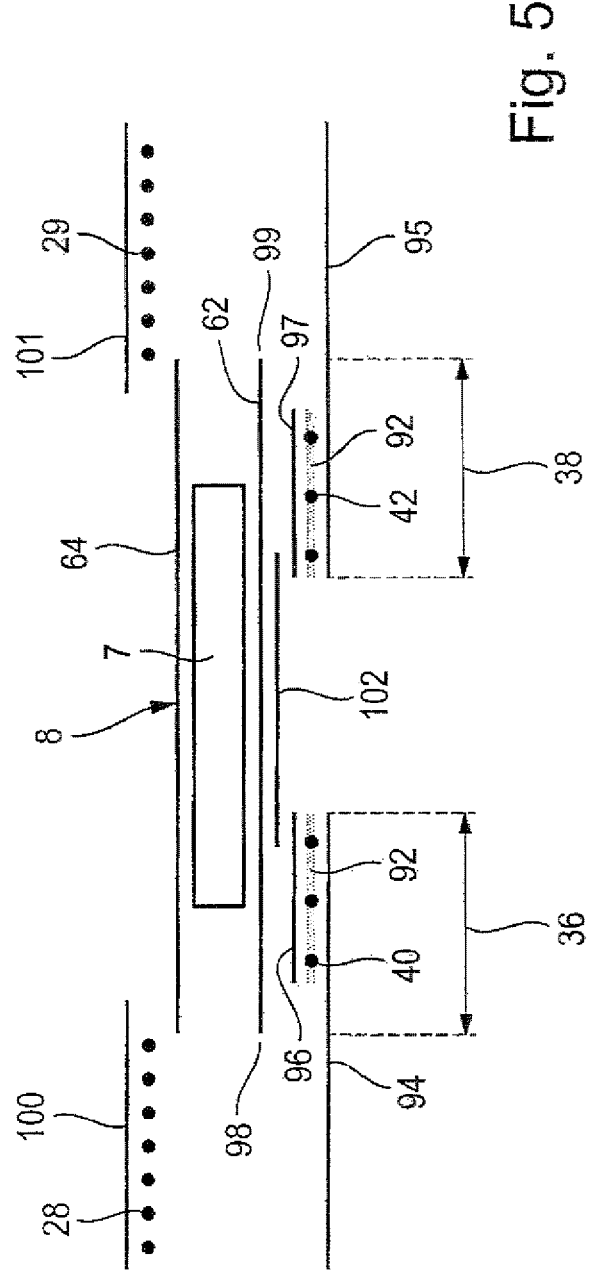

INCONTINENCE ARTICLE IN PANT FORM

CROSS-REFERENCES TO RELATED APPLICATIONS

This application claims the priority of German Patent Application, Serial No. 10 2012 208 395.2, filed May 18, 2012, pursuant to 35 U.S.C. 119(a)-(d), the disclosure of which is incorporated herein by reference.

This application claims the benefit of prior filed U.S. provisional Application No. 61/659,449, filed Jun. 14, 2012, pursuant to 35 U.S.C. 119(e), the disclosure of which is incorporated herein by reference.

BACKGROUND OF THE INVENTION

The invention relates to a folded incontinence article in pants form for absorbing bodily excretions.

The following discussion of related art is provided to assist the reader in understanding the advantages of the invention, and is not to be construed as an admission that this related art is prior art to this invention.

Incontinence articles in pants form principally differ from openable and closable incontinence articles in conventional diaper form, in that the waist circumference is already predetermined by the pant form, and the adjustment to different body sizes based on a number of basic sizes is achieved in that the article can be elastically stretched. For this, elastifying means, in particular the form of bands or threads, often also referred to as Lycra-bands are usually connected in pre-tensioned state (Stretch-Bond method) to chassis materials of the incontinence article i.e., they are fixed in a pre-tensioned state on the chassis materials for example by means of glue. Due to their pre-tension, these elastifying means bundle chassis materials together, thereby forming plications, which typically extend transverse to the direction in which the elastifying means are pre-tensioned, i.e. in this case in longitudinal direction of the article. The incontinence article or the elastified chassis materials of the incontinence article can then be elastically stretched again when the user puts on the incontinence article like a pant. In contrast, the chassis materials themselves are preferably not stretchable and can therefore be transported in a flat or even spread out state in the transport plane in a well defined manner, so that the elastifying means can then be attached with a well defined pre-tension.

Pant-shaped incontinence articles of the type here discussed are typically folded by the manufacturer and distributed to whole sellers or the end user in folded configuration, usually in foil bags with at least ten pieces.

As a result of the pant form, an incontinence article of the type discussed here already has a first folding axis in lateral seam regions after connection of the stomach section and the back section, which folding axis extends through the crest in the crotch of the pant. This first folding axis is formed in the manufacturing machine, and typically forms the first folding axis for the incontinence article which has to be folded further for distribution.

Because it is sought to realize a volume-efficient arrangement when folding the incontinence article preferably directly after its manufacture and separation in an endlessly operating manufacturing line, it was proposed to avoid multiple transverse foldings of the absorption body, for example in EP-A-123069 B1, JP-A-11-113956. According to EP-A-1 639 908 A1, two further foldings, which extend in transverse direction are required in addition to the first folding axis in the crest of the crotch region, likewise according to WO-A-2011/095908.

According to EP-A-1 140 662 a varying thickness in a folded the article is to be compensated in the packaging bag in that the article are arranged inverted in the stacking, likewise in EP-A-0 780 325 B1.

It would therefore be desirable and advantageous to provide a pant shaped incontinence article so that it can be folded optimally for distribution for sale, wherein overall a compact and evenly thick shape of the folded article and stack shaped arrangements formed therefrom which are then repackaged, can be realized.

SUMMARY OF THE INVENTION

According to one aspect of the present invention, an incontinence article in pant form for absorbing bodily excretions, includes a stomach section; a back section, spaced apart from the stomach section in a longitudinal direction of the incontinence article along a longitudinal center axis, wherein the stomach section and back section have respective lateral seam regions and are joined at the respective lateral seam regions thereby forming a stomach- and back band which is continuous in a transverse direction of the incontinence article, and has a circumferentially closed waist opening; a crotch section having an absorption body and extending in the longitudinal direction between the stomach section and the back section, wherein the crotch section overlaps with the stomach section and the back section in respective overlapping regions and is non-detachably connected to the stomach section and to the back section in the respective overlapping regions, wherein the stomach section, back section and crotch section together delimit leg openings of the incontinence article, wherein the stomach and back section have respective crotch-side regions facing the leg openings; first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacture, wherein the incontinence article has a first fold axis formed by a transverse center axis of the incontinence article, respective second fold axes provided outside the absorption body on either side of the absorption body and extending in the longitudinal direction, and a third fold axis provided in a region of the absorption body, wherein regions of the stomach section and the back section which laterally protrude over the crotch section are folded about the second fold axes in the direction toward the longitudinal center axis, wherein after folding the incontinence article about the third fold axis, a border of the stomach and back band does not protrude over the first fold axis, i.e. not over an outer folding edge of the incontinence article formed by the first folding axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis, where the absorption body has a mass per area that is at most 80% of the first mass per area.

Thus, a three-component incontinence article is involved, wherein the stomach section, the back section and the crotch section form these three components. The stomach section and the back section as well as the crotch section are fed into or transported in a manufacturing device as separate components. Typically, the components are guided in a respective transport plane in a flat or evenly spread out state. The stomach section and the back section are transported in the later transverse direction of the incontinence article; they are transported spaced apart in the later longitudinal direction of the incontinence article. Thus, the later transverse or waist-circumferential direction of the incontinence article extends in the machine direction of the manufacturing device. The aforementioned distance between the stomach section and the back section is then bridged by applying the crotch section as third component, wherein an overlapping region between crotch section and stomach section and between crotch section and back section is formed, wherein the three components are permanently joined with each other in the respective overlapping region. Finally, the stomach section and the back section are interconnected at lateral seam regions on both sides as mentioned above. Such an incontinence article is for example known from DE 10 2007 055 628 A1.

The position of the transverse center axis is selected so that it halves the longitudinal extent of the incontinence article between waist border of the stomach section and waist border of the back section in the stretched out flattened out state of the incontinence article (according to FIG. 1 or 7). In the following, this half longitudinal extent is referred to as L1. Also, all other here mentioned dimension or ratios of dimensions relate to the incontinence article shown in FIG. 1 in the flat stretched out state and its flat materials.

For determining the mass per area, a 25 mm×25 mm sized surface area is centered relative to the transverse center axis and the longitudinal middle axis, in which surface area the mass per area is analyzed. For measuring the mass per area, a 25 mm×25 mm large test specimen can be punched out of the absorption body in the direction of its thickness. For this, all layers of the absorption body between topsheet and backsheet are taken into account. For determining the mass per area, the test specimen is first dried 24 h at 105 C in a desiccation oven. After cooling down to room temperature, the test specimen is weighed to an accuracy within two decimal points on a precision scale.

According to the invention it is thus proposed to configure the absorption body with a variation of its mass per area of absorption body materials as set forth above, i.e. realizing a topography with regard to the amount and with this the mass per area of the absorption body materials in the described manner. It is further proposed to provide the third folding axis which extends in transverse direction and which beside the first folding axis is the only folding axis of the incontinence article extending in transverse direction, so that it extends through the absorption body. However, according to the invention it is proposed that this third folding axis extends through a region of the absorption body, in which the mass per area is reduced. In this way, it can be achieved that the folded incontinence article has no significant or interfering differences in thickness in its folded configuration. According to the invention this also allows achieving that the continuously elastified waist or back band does not protrude over the outer first folding edge of the incontinence article in an interfering manner. The waist and back band can advantageously extend, when viewed onto the folded incontinence article, essentially at least up to this outer folding edge. Therefore, it is not required that the folded pant-shaped incontinence articles have to be oriented inverted in the packaging bag. It is further advantageous that the individual folded incontinence article in the region of the outer edge which is formed by the third folding axis which extends in transverse direction, prove to be more graspable, i.e., they can also be removed easier from the packaging bag, because the end user grasps with his fingers (thumb up and other fingers down) onto the outside of chassis materials, which in this region are fixed with the absorption body there underneath, i.e., they cannot slip away.

The laterally protruding regions of the stomach and back ban are preferably folded about the respective second folding axis onto the stomach-side of the incontinence article. This is advantageous insofar as the back section usually extends more expansively in the longitudinal direction and the surface wise more expansive regions of the back section overlap the less expansive regions of the stomach section. On one hand, this achieves a visually appealing folding and on the other hand prevents that a multitude of material ends is perceivable from the outside, which would cause the further packaging process to be more prone to errors.

It is further advantageous, when the mass per area of absorption body material in the region of the third folding axis is at most 70%, in particular at most 60%, in particular at most 50%, in particular at least 20%, in particular at least 30% of the value of the first mass per area.

It is further especially advantageous when the mass per area of absorption body material, starting from the transverse center axis along a longitudinal center axis in the direction toward the stomach-side end of the absorption body and/or in the direction toward the back-side end of the absorption body decreases stepwise, so that stepped plateaus are formed. It is noted at this point that the variation in mass per area of absorption body material does not necessarily have to correspond to a corresponding variation in size of the topographical three-dimensional form or shape, i.e., to the respective thickness of the absorption body. Typically the absorption body materials are compressed and compacted in the manufacturing machine after the in particular multi-step deposition by calendar rolls. Nevertheless, the mass per area of the absorption body material significantly influences the behavior of the incontinence article during folding and its subsequent folded configuration.

When the mass per area decreases stepwise, the regions bordering a step can be seen or represented in a top view onto the evenly spread out state of the absorption body (as shown in FIG. 1) as surfaces or plateaus extending two-dimensionally in the drawing plane. These surfaces or plateaus do not necessarily have an even mass per area of absorption body material, but can be more or less "inclined" from one step to the next, i.e., have a decreasing mass per area in the direction toward the ends of the absorption body. However, an absorption body topography in which the mass per area is even in between stepwise decreases in the direction toward the longitudinal center axis are preferred.

In a further concretizing of the idea of the stepwise decrease of the mass per area of the absorption body material, it is proposed that the plateaus are delimited by straight step-shaped transitions, which extend in transverse direction.

It is further proposed that the absorption body has longitudinal borders, which extend straight and in longitudinal direction. This means, that according to a preferred embodiment of the present invention, the absorption body has the shape of a rectangular strip when viewing onto the evenly spread out state from the top (FIG. 1). This strip is preferably significantly narrower in transverse direction than the width of the crotch section, so that sufficient space remains outside the absorption body for upright cuff elements and leg-elastifying means. Further advantageous are straight, longitudinal borders, because in this case no lateral ears of the absorption body protrude laterally, which would interfere with the longitudinal folding about the second folding axes.

It is further proposed to configure the absorption body so that it has multiple plateaus in its stomach-section side half and/or in its back-section side half, wherein the mass per area of the plateaus of absorption body material starting from the transverse center axis in each case along a longitudinal center axis in the direction toward the stomach-section side end of the absorption body and in the direction toward the back-section side end of the absorption body decreases from one plateau to another. Such a configuration allows constructing the absorption body with multiple layers in the direction of its thickness, i.e. with discrete layers. In this context, it is especially advantageous when the absorption body has a first basic layer and thereon a second absorption body layer which has a three-dimensional topology across its extent as a result of variations of mass per area, and preferably thereon an hour-glass-shaped, body-facing liquid-absorption and distribution layer. The mentioned basic layer can advantageously have a uniform mass per area across its extent. The absorption body layer arranged there above is recessed in the longitudinal direction and preferably also in the transverse direction relative to the basic layer. The recess is typically greater on the stomach-section side half of the incontinence article than on the back-section side half. On the stomach-section side half, the recess is in longitudinal direction between 10 and 50 mm, in particular between 20 and 40 mm, in particular between 25 and 40 mm and in the back section—side have in longitudinal direction in particular between 5 and 20 mm, in particular 5 and 15 mm.

According to a particularly relevant further inventive idea it is advantageous, when the first mass per area of the absorption body starting from the transfer center axis in each case along the longitudinal center axis in the direction toward the stomach-section side end of the absorption body and in the direction towards the back-section side end of the absorption body remains essentially constant over an extent of at least 20%, in particular of at least 30%, in particular of at most 70% and further in particular of at most 60% of the distance of the transverse center axis to the stomach-section side end of the absorption body or to the back-section side end of the absorption body. In this context, the feature "essentially constant" means that the variation or deviation from the mean value (maximal mass per area minus minimal mass per area) is at most 5%.

It is further advantageous when the longitudinal extent of a plateau, which adjoins a step in the stomach section—side part and/or in the back section—side part of the absorption body in longitudinal direction and through which the third folding axis extends, is at least 50%, in particular at least 20%, in particular at most 50%, in particular at most 40%, in particular at most 30% of the distance of the transverse center axis to the stomach-section side end of the absorption body or to the back-section side end of the absorption body.

Starting from the longitudinal center axis, the absorption body can have a mass per area of absorption body material, which decreases in transverse direction. Preferably, the mass per area of absorption body material does not increase in transverse direction.

It is advantageous, when the third folding axis in the stomach section and in the back section extends through a respective end section of the absorption body, wherein a respective end section covers at most $\frac{1}{5}$, in particular at most $\frac{1}{6}$ and further in particular at most $\frac{1}{7}$ of the longitudinal extent of the absorption body.

It is further advantageous when the third folding axis extends in the overlapping region of crotch section and back section and/or in the overlapping region of crotch section and stomach section. This achieves, that the respective stomach—or back section completely covers the region of the outer folding edge of the incontinence article in the region of the third folding axis, which is optically and tactilely advantageous.

In a preferred embodiment of the folded incontinence article according to the invention, it is advantageous that the thickness measured under a test pressure of 20 g/cm$^2$ at three different sites, namely in the region which is spaced apart from the border that is associated with the first folding line by 10 mm, and in a region that is spaced apart from the border associated with the third folding access by 10 mm, and in a region located there between, the longitudinal direction in each case deviates by less than 6%, in particular less than 5%, in particular less than 4%, in particular less than 3% from a mean value of the measurements at the three sites. For determining the thickness of the folded incontinence article, test specimens are punched out of the entire folded incontinence article, which have a longitudinal extent of 50 mm and extend over the entire transverse direction of the folded article. These test specimens are arranged centered opposite a testing die of 100×100 mm and subjected to a test pressure off 20 g/m$^2$. Even though the thickness strongly depends from the duration of the pressure testing, the thickness is measured after 30 minutes of load. For determining the thickness values of each of the three regions, three respected folded articles are taken into account based on the respected arithmetic mean of the measurement values. The thickness of the folded incontinence article at the three sites can be 14 to 25 mm, in particular 14 to 22 mm, in particular 14 to 20 mm, in particular 14 to 18 mm.

With regard to a compact folding, it is especially advantageous when the extent (L2) of the respective lateral seam in longitudinal direction is 100-170 mm and when the ratio (L2/L1) between the extent (L2) of the respective lateral seam in longitudinal direction and the extent (L1) of the incontinence article between border of the stomach- and back band and a transverse center axis is at most 0.42, in particular at most 0.4, in particular at most 0.39, in particular at most 0.38 and further in particular at least 0.20, further in particular at least 0.25, further in particular at least 0.30. In typical sizes, the longitudinal extent L1 of the incontinence article discussed here, is 322 450 mm, in particular 330 to 440 mm and further in particular 342 4030 mm.

In this context, it is also advantageous when in the stomach section and in the back section the ratio (L4/L1) of the distance (L4) of the outermost waist-facing first elastifying means in longitudinal direction to the innermost crotch-facing first elastifying means and the extent (L1) of the incontinence article between waist border and the transverse center axis is at most 0.3, in particular at most 0.29 in particular at least 0.12, in particular at least 0.15, in particular at least 0.18.

It is further contagious, when in the stomach section and/or the back section the ratio (d1/L4) between the distance (d1) of the first elastifying means longitudinal direction to one another and the distance (L4) of the outermost waist-facing first elastifying means in longitudinal direction to the innermost crotch-facing first elastifying means is between 0.08 and 0.5, in particular between 0.09 and 0.20, in particular between 0.10 and 0.18. It is advantageous when the distance (d1) of the first elastifying means in longitudinal direction to one another is at least 8 mm, in particular at least 10 mm, in particular 10-15 mm, in particular 11-14 mm, further particular 12-13 mm.

Preferably, thread-shaped or band-shaped elastifying means such as rubber threads, polyetherpolyurethane threads or polyesterolyurethane threads, preferably elastic threads such as Lycra®- or Spandex® threads are used as first and/or second elastifying means.

It is further advantageous, when the thread strength of the first elastifying means is at least 1000 dtex, in particular at least 1100 dtex, in particular at least 1200-1500 dtex, in particular 1200-1400 dtex and/or when the thread strength of the second elastifying means is 500-1100 dtex, in particular 600-1000 dtex, in particular 700-900 dtex. The thread strength of the first elastifying means is preferably greater than the thread strength of the second elastifying means.

The thread strength of the elastifying means is expressed in the unit dtex (1 dtex=1 g/10,000 m). The thread strength is determined according to the testing guidelines BISFA, the International Bureau for the Standardization of man-made Fibres, Test methods for bare elastane yarns, edition 1998, chapter 5: "Determination of linear density". The thread strength or linear density is determined by determining the mass of a test specimen having a known thread length of 1,000 mm (cut under a standard pre-tension of 0.1+/−0.01 mN/dtex) after a conditioning under standard conditions (23° C.+/−2° C., 50%+/−5% relative humidity) in the relaxed state.

The thread strength (in dtex) is calculated from the quotient of the mass (in g) divided by the length of the section (in m) multiplied by the factor 10,000.

For this, five sections of the thread-shaped or band-shaped elastifying means having a length of 1,300 mm are cut off from the role or package under a tension that is as small as possible, namely in uneven distances of at least 2 m. These five sections are relaxed so as to be tension-less and are let rest under standard conditions for at least four hours. Then, a test specimen of 1,000 mm+/−1 mm is cut off from the respective 1,300 mm long section, while the section is maintained under a pre-tension of 0.1 mN/dtex. The cut off test specimens of 1,000 mm length are weighed to an accuracy of +/−1% of their expected mass. For each testing specimen, its thread strength is obtained by multiplying the respective mass with the factor 10,000 in dtex. From the five testing specimen, the arithmetic mean value is calculated which is used as thread strength for the purposes discussed here.

The pre-tension is defined as the degree of stretching of a stretched elastifying means relative to the unstretched/relaxed original state of the elastifying means in the state of the application and fixing of the elastifying means in the manufacturing machine. The degree of stretching is thus calculated as the ratio of the stretched length L' (=initial length L+ΔL) to the initial length L, i.e., L'/L.

As mentioned, the first and second elastifying means are fixed in the pre-tensioned state relative to the chassis materials (Stretch-Bond-Method) for achieving a return force and with this a two-dimensional elastification of the stomach section and the back section. In this regard it is advantageous when the first elastifying means are fixed with a pre-tension which is greater than a pre-tension with which the second elastifying means are fixed by the factor 1.1, in particular at least 1.2, in particular at least 1.3, and in particular at most 2.0, in particular at most 1.8, in particular at most 1.6. In this regard it is advantageous when the first elastifying means are fixed with a pre-tension of 3-8, in particular 3-7, in particular 4-7 and further in particular 4-6 and/or the second elastifying means are fixed with a pre-tension off 2-5, in particular 2.5-4.5, in particular 2.5-4 and further in particular 3-4.

According to a further independent invented idea it is advantageous, when the crotch section is non-detachably connected with the stomach section and the back section by adhesive strips which are provided in the overlapping region of crotch section and stomach and in the overlapping region of crotch section and back section and extend in transverse direction and parallel to one another and are spaced apart by adhesive-free strips, wherein the adhesive strips essentially cover the entire respective overlapping region, and when the width at least of those adhesive strips which are located inwardly relative to optional border side adhesive strips transverse to their extent is at least 1 mm to at most 5 mm, and when the width of the adhesive-free strips transverse to their extent is at least 1 mm to at most 15 mm. This connection of the crotch section with the stomach section and the back section results in a preferred direction which extends in transverse direction and which facilitates the folding of the incontinence article about the third folding axis which extends in the transverse direction. This can be explained in that the strip-shaped applied glue can enter into the three-dimensional porous, mostly nonwoven-based chassis materials, and thus leads to a stiffening and structuring in the transverse direction.

Further in particular visually and/or tactilely perceivable structures are formed in transverse direction on the outer visible side of the incontinence article in the overlapping region of crotch section and stomach section and in the overlapping region of crotch section and back section, which structures correspond to the course of the adhesive strips and the adhesive free strips.

These visually and/or tactilely perceivable structures are particularly advantageous in the folded state of the incontinence article because it results in the formation of a grippy edge region in the region surrounding the third folding axis, which extends in the transverse direction.

In a refinement of this inventive idea it is advantageous when in the overlapping region of crotch section and stomach section and/or in the overlapping region crotch section and back section two outer border side adhesive strips, and in longitudinal direction between these border side adhesive strips, multiple inwardly located adhesive strips are provided, wherein the width of the border-side adhesive strips is greater then the width of the inwardly located adhesive strips, and is in particular at least 4 times, in particular at least 5 times, and further in particular at most 8 times, in particular at most 7 times the width of the inwardly located adhesive strips.

The chassis-forming materials of the stomach section and/or back section preferably include nonwoven materials such as spunbonds, card webs or through air bonded card webs. Particularly preferably, the chassis forming material of stomach section and/or back section includes a spunbond material. The nonwoven materials that are used for the stomach section and/or back section Preferably have a mass per area of 10-30 g/m$^2$, further preferably of 15-25 g/m$^2$. Particularly preferably the stomach section and the back section include a spunbond, in particular made of polypropylene, in particular with a mass per area of 15-25 g/m$^2$.

The crotch section advantageously includes a liquid-impermeable backsheet-material and a nonwoven topsheet material. The backsheet material in particular includes a foil, in particular with a mass per area of 8-20 g/m$^2$, in particular 8-16 g/m$^2$, further in particular 8-14 g/m$^2$. In particular, the backsheet includes a foil which in particular is micro-porous and during use liquid-tight but at the same time breathable, i.e. permeable for water vapor.

The invention also relates to a packaging bag, which is filled with incontinence articles which are folded and configured according to the invention.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 5 shows a schematic sectional view of the relevant individual components of the chassis materials along the longitudinal center axis of the incontinence article;

DETAILED DESCRIPTION OF PREFERRED EMBODIMENTS

Figure 1:
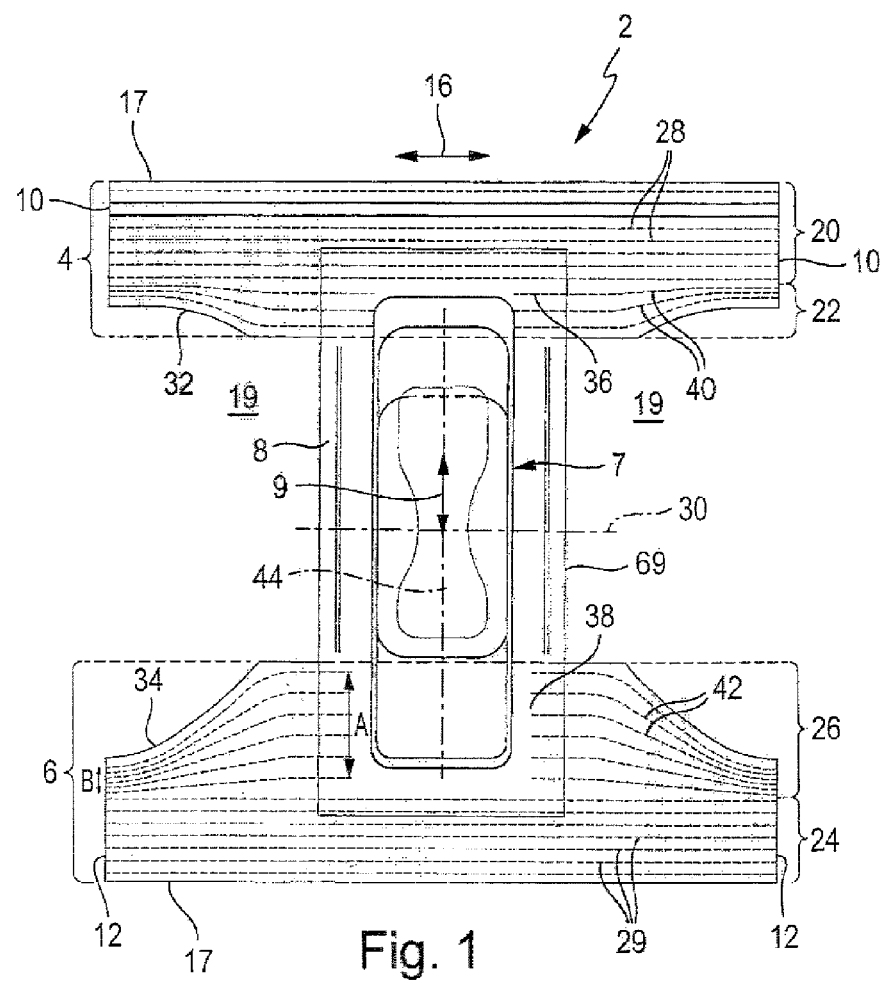
FIG. 1 shows a top view onto an incontinence article according to the invention, wherein a stomach section, a back section and a crotch section of the incontinence article are not yet joined for forming a pant form but are shown in a spread out and evenly stretched out state.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

The Figures show an incontinence article in pant form, overall designated with the reference numeral 2, for absorbing solid and liquid bodily excretions. The incontinence article 2 is composed of three components which can essentially be manufactured independently i.e., a front stomach section 4, a rear back section 6, and a crotch section 8 which has an absorption body 7 and is located between the stomach section 4 and the back section 6, wherein the crotch section 8 extends in a longitudinal direction 9 of the incontinence article 2 and overlaps with a substantial surface portion of the stomach section 4 on one hand, and of the back section 6 on the other hand, and is non-detachably connected by the manufacturer in the overlapping region in a manner to be described in more detail below. As can be seen from FIG. 1, this leads to an H-shaped basic structure of the incontinence article. For forming the pant form, the interconnected components shown in FIG. 1 are then connected to one another at respective lateral longitudinal border sections 10, 12 of the stomach section 4 and the back section 6, also by the manufacturer, by conventional joining methods, thereby forming lateral seam regions 14 on both sides. In this pant form of the incontinence article, which is manufactured by the manufacturer, the stomach section 4 and the back section 6 extend in a transverse- or waist-circumferential direction 16 continuously and thus define with their waist border 17 a waist opening 18 which is closed in waist-circumferential direction; further, together with the crotch section 8 they delimit leg openings 19, through which the user can put on the incontinence article like a pant.

The stomach section 4 can be divided into a waist-side region 20 and into a crotch-side region 22, which faces the leg openings 19. The back section 6 can be divided correspondingly i.e., also in a waist-side region 24 and a crotch-side region, which faces the leg openings 19.

In the waist-side region 20 of the stomach section 4 and in the waist-side region 24 of the back section 6, first elastifying means 28, 29 are provided, which may be Lycra-threads, and which are connected with the flat materials (chassis materials) of the stomach section 4 and the back section 6 in the so-called stretch-bond-method. These first elastifying means 28, 29 extend in transverse- or waist-circumferential direction 16 from one lateral seam region 14 to the other.

The respective crotch-side sections 22 and 26 of the stomach section 4 or of the back section 6 which face the leg openings 19 each have a border contour 32 or 34 which deviates from the transverse- or waist-circumferential direction 16 and which extends towards a transverse center axis 30 of the crotch section 8. This border contour 32, 34 is also arch-shaped in the representation according to FIG. 1 and therefore suited for delimiting the leg openings 19.

Through this extent of the crotch-side region 22 or 26 which faces the leg openings, a relatively great overlapping region 36, 38 between the crotch section 8 and the stomach section 4 or back section 6 is realized, which is important with regard to a tear-resistant connection of crotch section 8 and stomach section 4.

The respective crotch-side region 22, 26 of the stomach section 4 or the back section 6 which crotch-side region 22, 26 faces the leg openings 19, is also configured elastified and is provided with second elastifying means 40 or 42. The second elastifying means 40, 42 extend, in each case starting from the lateral seam regions 14, in the direction towards a longitudinal center axis 44 of the incontinence article. As can be seen from FIG. 1, the second elastifying means 40, 42 fan out in the direction towards the longitudinal center axis 44, i.e., with increasing distance to one another in the direction towards the longitudinal center axis 44. The second elastifying means 40, 42 pass underneath the crotch section 8. In the region below the absorption body 7, they may be deactivated i.e. they may not posses their elastifying effect.

Figure 2A:
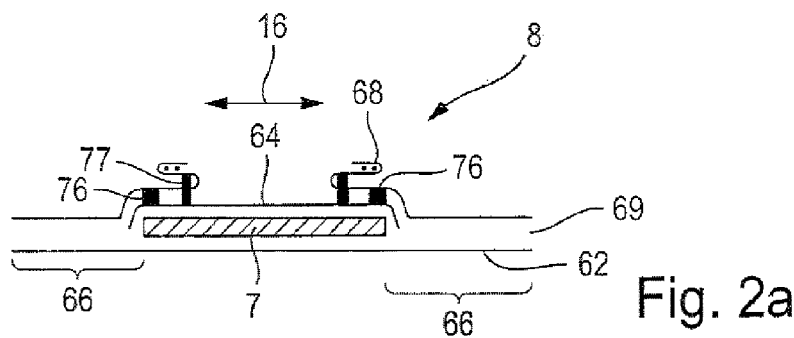
FIGS. 2 a, b show schematic sectional views of the crotch section in the region of the transverse centerline or in the overlapping region of crotch section and back section.
Figure 2B:
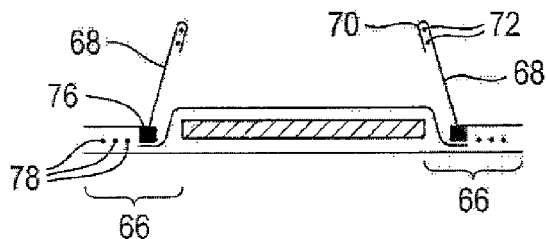

As can be seen from FIGS. 2 a,b, the crotch section 8 includes a liquid-impermeable backsheet material 62, which can in particular be formed by a breathable, but liquid-tight foil material and a preferably nonwoven-based topsheet material 64. The absorption body 7 (only shown schematically) is arranged between the backsheet material and the topsheet material. In the exemplary shown case, the backsheet material 62 forms an overhang 66 over the absorption body 7 in transverse direction 16. The topsheet 64 protrudes over the absorption body 7 in transverse direction 16 only to a relatively small degree and an upright barrier means 68 is provided on both sides of the absorption body 7. The barrier means 68 extends in a longitudinal direction 9, and is typically referred to as upright cuff element and is preferably made of a hydrophobic, in particular liquid-impermeable nonwoven material which extends in transverse direction 16 as far as to lateral longitudinal borders 69 of the crotch section 8. The distal ends 70 of the barrier means 68 are provided with further elastifying means 72 which raise the barrier means 68 during use of the incontinence article relative to the skin surface of the user. The lateral barrier means 68 are fastened on the topsheet 64 or onto themselves in a C-shape-folded configuration via schematically indicated fixations 76, 77. Outside of the absorption body 7 i.e., in the region of the protrusion 66, leg-elastifying means 78 are provided, which preferably extend at a defined distance to the material-rich and with this rather bending stiff absorption body 7, in order on one hand, to prevent exerting additional stretching or distortion forces on the absorption body, which might negatively influence the absorption properties of the absorption body and on the other hand to realize a liquid-tight leg sealing, which to the most degree is not influenced by the absorption body. These leg-elastifying means 78 end in longitudinal direction 9 at a significant distance of in particular 10 mm, preferably at least 20 mm before the second elastifying means 40 and 42 of the stomach section 4 or the back section 6. Preferably, these leg-elastifying means 78 end in longitudinal direction 8 before the stomach section 4 and the back section 6.

Figure 4:
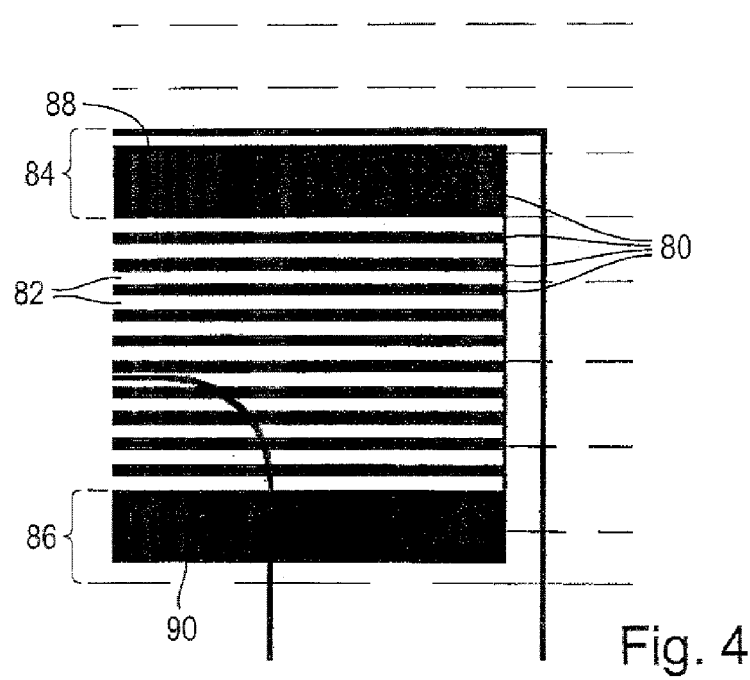
FIG. 4 shows an enlarged representation of a section in the region of the overlapping region of crotch section and stomach section or crotch-section and back section of the incontinence article according to FIG. 3.
Figure 3:
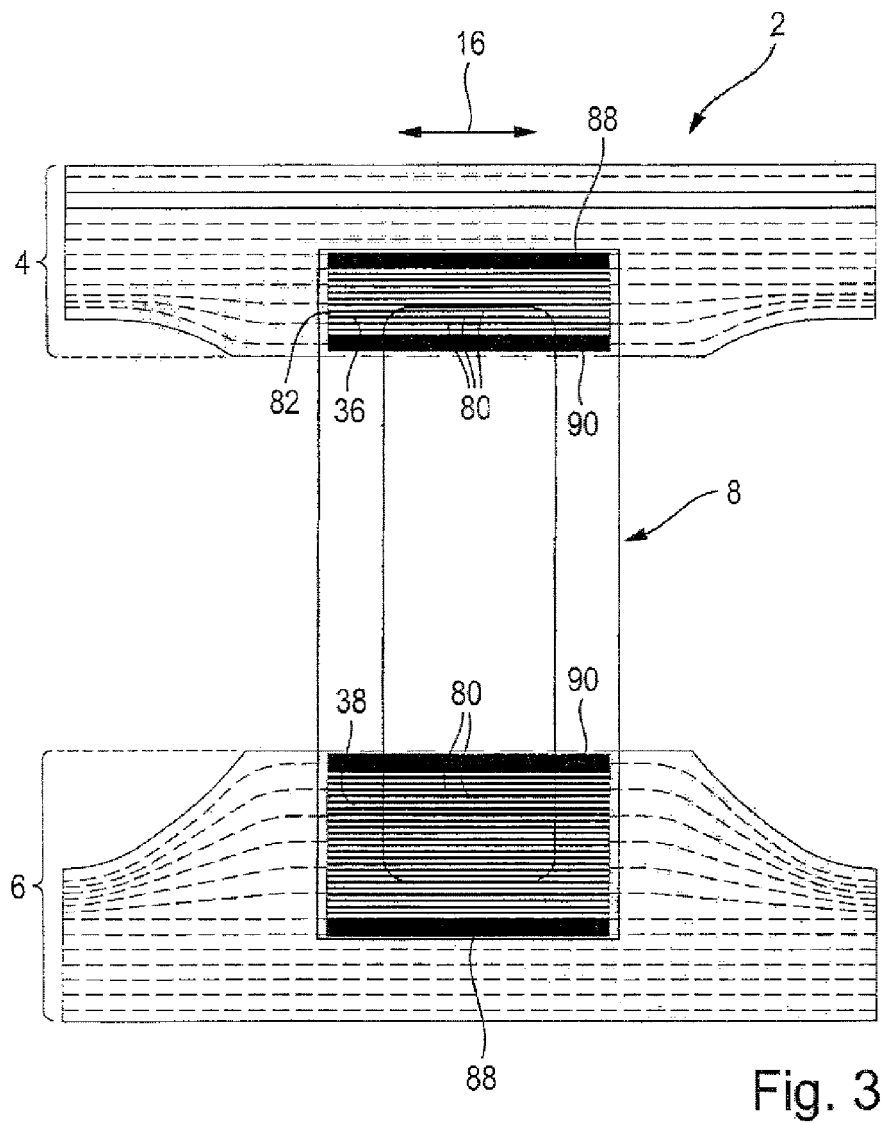
FIG. 3 shows a representation corresponding to FIG. 1, illustrating the fixing of the crotch section with the stomach section and the back section by means of adhesive strips.

In the following, the fixing of the crotch section 8 in the front overlapping region 36 with the stomach section 4 and in the rear overlapping region 38 with the back section 6 is described. As can be seen in FIGS. 3 and 4, for this purpose, adhesive is not applied to the entire surface, but multiple adhesive strips 80 are provided in the overlapping region and extend in transverse direction 16 and parallel to one another and are spaced apart by adhesive-free strips 82. The adhesive strips 80 occupy or overlap essentially the entire respective overlapping region 36, 38. In the exemplary shown, however, not strictly required case, broader adhesive strips 88 and 90 are provided in a border region 84 and a border region 86 of the respective overlapping region 36, 38, which border region 84 is located waist-side in longitudinal direction and which border region 86 faces away from the waist in longitudinal direction. The respective border-side i.e., waist-facing and waist-distal adhesive strips 88, 90 have a greater width than the multitude of adhesive strips 80 which are located inwardly and between the adhesive strips 88, 90. In an exemplary embodiment, the width of the border-side adhesive strips 88, 90 transverse to their extent is 14 mm, the width of the inwardly located adhesive strips 80 is 2 mm and the width of the adhesive-free strips 82 is 3 mm. In the exemplary and preferred shown case, the inwardly located adhesive strips 80 preferably all have the same width and the distances between them i.e., the width of the adhesive free strips 82 are preferably also the same. Nevertheless, the same explanations set forth in the beginning apply with regard to the dimensions and the conditions described there, as well as with regard to the mass per area of the adhesive coating of the adhesive strips. The surface of the front and rear overlapping region 36, 38 relative to the surface of the stomach section 4 or the back section 6 also lies within the previously explained preferred ranges.

It can further be seen from FIG. 3 in conjunction with FIG. 1 that the second elastifying means 40, 42 in the respective overlapping region 36, 38 extend parallel to the adhesive strips 80. In the exemplary shown case, some of the first elastifying means 28 also extend in the front and rear overlapping region 36, 38 (however on the body-facing side of the crotch section). The second elastifying means 40, 42 were also introduced so as to be continuous in the transverse direction 16; they are de-elastified in the respective overlapping region 36, 38 by the aforementioned measures. Even though the second elastifying means remain visible also in the de-elastified state—as explained above, they are concealed by the multitude of adhesive strips 80, thereby reducing their visibility.

In the preferred shown case, the second elastifying means are fixed in a glue bed 92 between chassis material layers 92 and 96 or 95 and 97 (c.f. FIG. 5). The glue bed 92 is applied on one of the chassis material layers 94, 96 or 95, 97. Then, the second elastifying means 40, 42 are placed on or introduced preferably in an endless manner and covered and laminated by the further chassis material layer. In this way, the second elastifying means 40, 42 are fixed and the chassis material layers 94 and 96 or 95 and 97 are joined to each other over their entire surfaces. The body-averted chassis material layer 94, 95 is a breathable fiber nonwoven material, which corresponds to the extent of the stomach section 4 or back section 6. The chassis material layer 96, 97 is an inwardly located fiber nonwoven material which is recessed relative to the chassis material layer 94, 95. In the preferred shown case, it ends in longitudinal direction 9 before the longitudinal end 98, 99 of the crotch section 8.

In the exemplary and preferred shown case, the first elastifying means 28, 29 are fixed between the body averted chassis material layer 94 or 95 and a further body-facing chassis material layer 100, 101 by single-strand application of adhesive. The further chassis material layer 100, 101 is again formed by a nonwoven material. The body-averted and the body-facing chassis material layers are exclusively interconnected by the first elastifying means 28, 29 to which adhesive has been individually applied i.e., only along the extent of these first elastifying means 28, 29. The skin friendly nonwoven materials are therefore not fixed to one another over their entire surfaces, but can detached from one another and, in particular as a result of the elastifying effect, can form pleatings and cuffs. In the preferred shown case, the body-facing chassis material layer 100, 101 extends in the stomach section 4 as well as in the back section 6 over the respective longitudinal end 98, 99 of the crotch section 8 on its body facing-side. It thus overlaps this material transition and in this way prevents an unevenness that leads to skin irritation.

Further, it can be seen in FIG. 5 that the backsheet 62 of the crotch section 8 has a coating 102 on its body-averted side. This coating 102 is a fiber nonwoven coating of the substantially liquid-impermeable backsheet 62. The coating 102 extends in longitudinal direction 9, however, not over the entire longitudinal extent of the backsheet 62 but instead ends relatively short within the front and rear overlapping region 36, 38. Outside of the overlapping region, the coating 102 is provided over the entire extent of the body-averted side of the back sheet 62. The coating 102 is preferably composed of a nonwoven material, in particular of a spunbond material, in particular of polypropylene, in particular with a mass per area of 10-20 g/m$^2$, in particular of 12-17 g/m$^2$.

Figure 6:
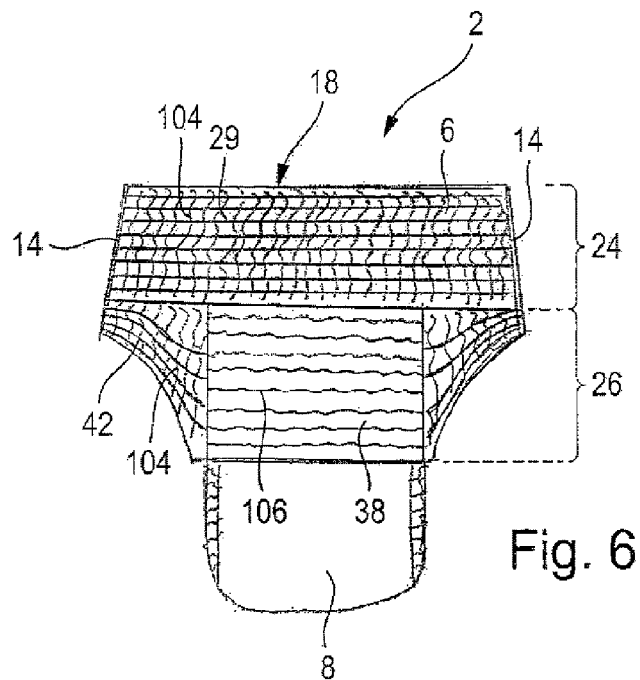
FIG. 6 shows a schematic view of the incontinence article in its final configuration.

FIG. 6 shows a schematic view of an incontinence article according to the invention in the finished configured state in which the stomach section 4 and the back section 6 are joined to one another, forming lateral seam regions 14. Only schematically shown are pleatings or cuffs 104 formed as a result of the contracting effect of the first and second elastifying means 28, 29, 40, 42, resulting from the fixing of the elastifying means in the pre-tensioned state on the chassis materials (stretch bond method). As a result of the multitude of relatively fine adhesive strips 80 in the respective overlapping region 36, 38 of crotch section 8 and stomach section 4 or back section 6, a visually and/or tactilely perceivable structure 106 is formed in the outer visible side of the incontinence article in the respective overlapping region 36, 38 which is here only shown as outline. According to the invention, it was found that the adhesive applied in strip-shape enters into the three-dimensional porous and also breathable configured fiber nonwoven materials, which are typically used as chassis materials, and leads to such an optical and/or tactilely perceivable structure 106, which can be advantageous as mentioned before. In addition, the connection of the crotch section 8 and stomach section 4 or back section 6 by the multitude of relatively narrow adhesive strips 80 leads to a very cost-effective use of adhesive while at the same time nevertheless providing the required holding forces for securely joining the three components to one another.

Figure 7:
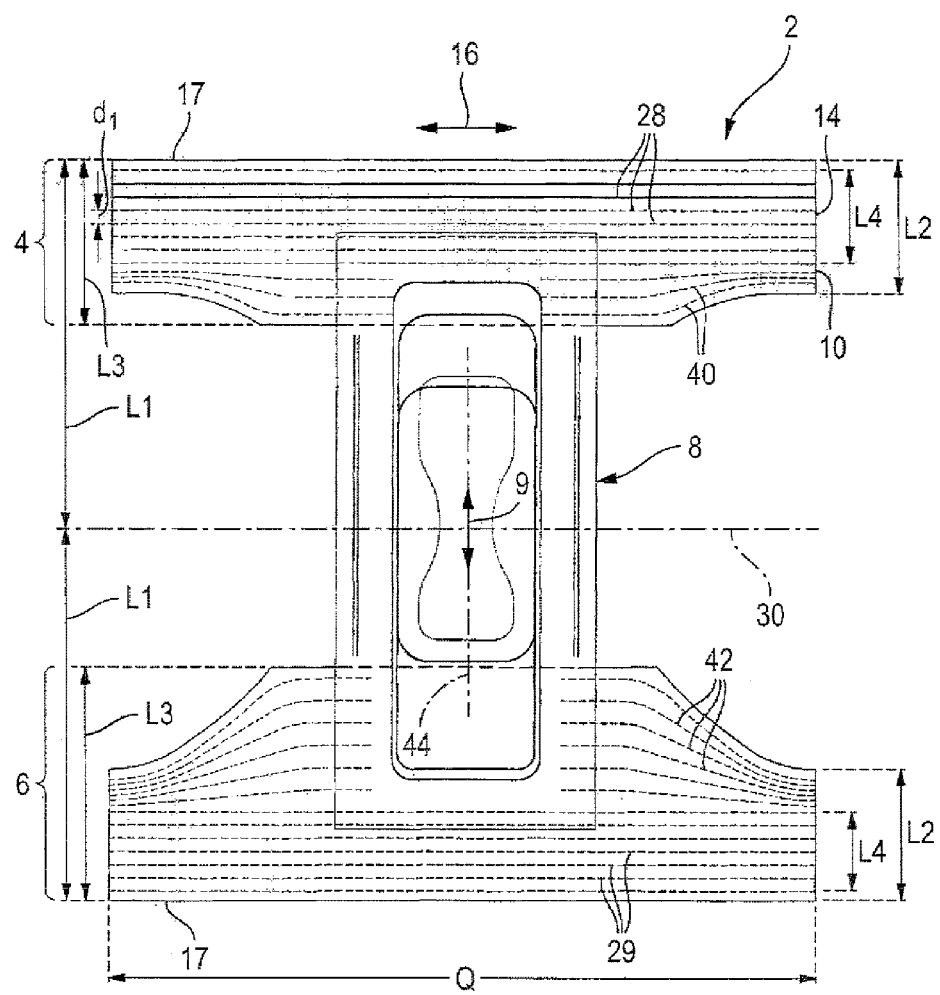
FIG. 7 shows a representation corresponding to FIG. 1, illustrating dimensions.

FIG. 7 explains the measurements, dimensions and ratios of the incontinence article according to the invention. It can be seen that the position of the transverse center axis 30 divides the overall length of the incontinence article in half in the flatly spread out state (according to FIG. 1). The transverse center axis 30 also forms a first folding axis 16 which extends in transverse direction 16, and about which the components are folded inside the manufacturing machine in order to arrange the longitudinal border sections 10, 12 of the stomach section 4 and back section 6 on top of one another for fixing and forming lateral seam regions 14 on both sides. Typically, this occurs by guiding endless, flat materials, which form the respective stomach section 4 and back section 6 i.e., even before the separation of the articles. The length L1 between the transverse center axis 30 and the respective border of the waist 17 can be seen. Further, the extent L2 of the respective lateral seam or the lateral seam region 14 in longitudinal direction 9 can be seen, which also corresponds to the length of the respective longitudinal border section 10 at 12. According to the invention, the ratio L2/L1 is at least 0.42.

Further, the distance L4 of the outermost waist-facing first elastifying means 28, 29 in longitudinal direction 9 to the innermost crotch-facing first elastifying means 28, 29 can be seen. According to the invention, the ratio L4/L1 is at most 0.3.

It can further be seen, that the first elastifying means 28, 29 have a distance d1 to one another, which is at least 20% greater than the distance of the second elastifying means 40, 42 to one another defined in the lateral seam region 14. In the preferred shown case, the first elastifying means 28, 29 all have the same distance d1 to one another, which is at least 10 mm, in particular 10 to 15 mm. The ratio d1/L4 is preferably 0.08 to 0.25.

Further, L3 can be seen as the extent of the stomach section 4 and back section 6 in longitudinal direction 9, which for the stomach section 4 is in particular 135-260 mm and for the back section 6 in particular 200-320 mm.

Further shown is the extent Q of the stomach section 4 or the back section 6 in transverse direction 16, which enters into ratios L2/Q or L4/Q.

The first elastifying means 28, 29 have a thread strength, which is at least 20% greater than the thread strength of the second elastifying means 40, 42. In addition, the first elastifying means 28, 29 are fixed with a pre-tension with the chassis material layers in the stomach section 4 and in the back section 6, which pretension is 10% greater than that of the second elastifying means.

Reference is made to the further preferred afore described measurements, dimensions and ratios.

Figure 8:
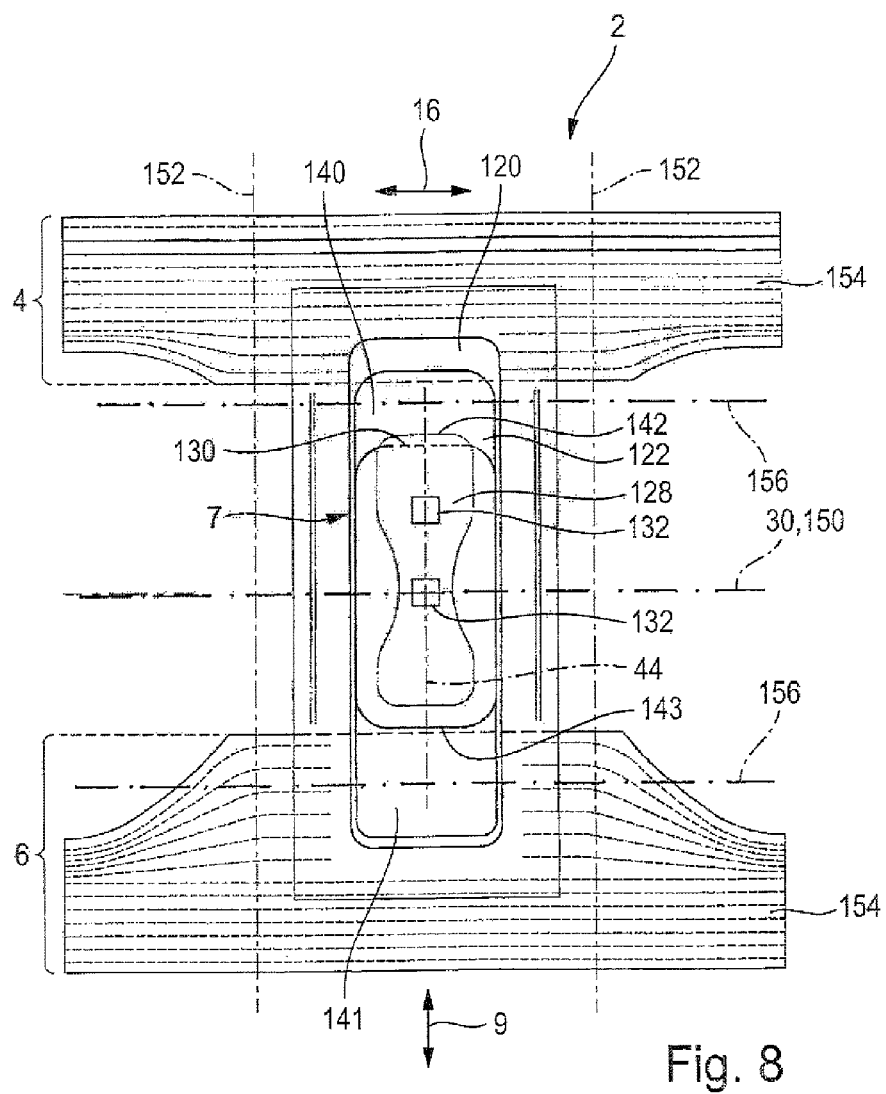
FIG. 8 shows a representation corresponding to FIG. 1, illustrating the construction of the absorption body and the folding axes.
Figure 9:
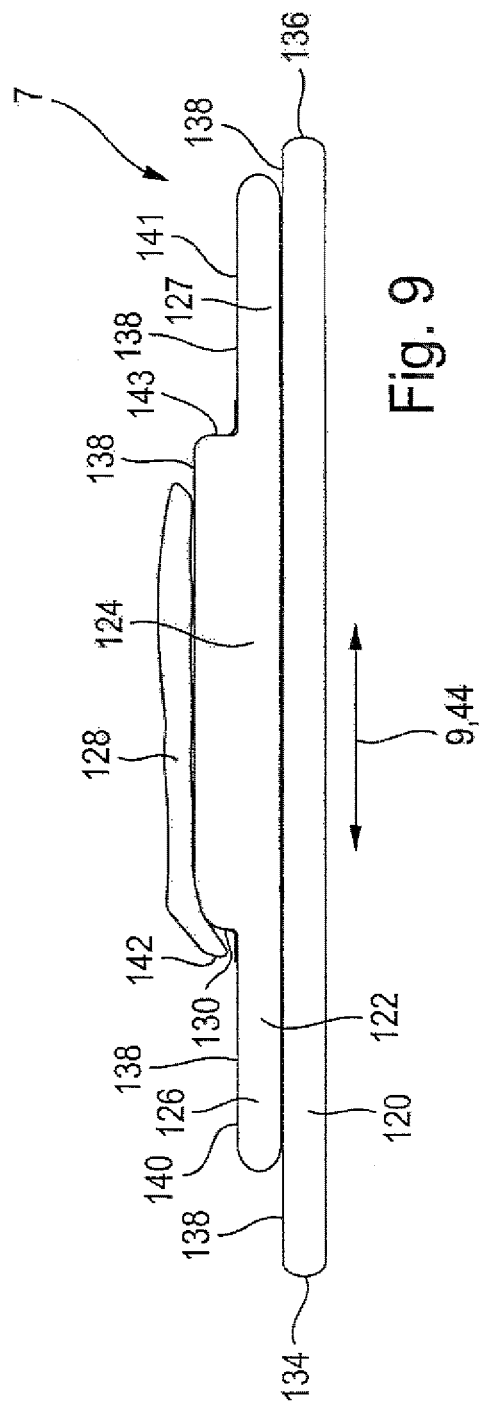
FIG. 9 shows a schematic longitudinal sectional view of the absorption body taken along the longitudinal center axis.

FIGS. 8 and 9 show the construction of the absorption body 7 in a top view and in a sectional view along the longitudinal center axis 44. Starting from its body-averted side, the absorption body 7 includes a basic layer 120 made of cellulosic fiber material with an exemplary mass per area of 176 g/m². Depending on the exact two-dimensional extent, the basic layer contains 10 to 14 g of cellulosic fiber material.

On the basic layer 120, an absorption body layer 122 is placed, which is three-dimensionally shaped at least with regard to the mass per area of absorption body material. In a center region 124, the absorption body layer 122 has a higher mass per area of absorption body material then in front and rear regions 126, 127, in longitudinal direction 9. In the exemplary shown case, the mass per area of cellulosic fiber material in the front and rear region 126, 127 of the absorption body layer 122 is 162 g/m² and in the center region 124 329 g/m². In addition, the absorption body layer 122 includes overall about 7 g of superabsorbent polymer materials, which are homogenously, evenly distributed in the absorption body layer 122. The regions 126, 127 and 124 are offset backward in longitudinal direction 9 relative to the two-dimensional extent of the basic layer 120 as can be seen from FIG. 8.

Finally, the absorption body 7 includes a body-facing liquid-absorption and distribution layer 128, which in the exemplary and preferred shown case has an hour class-shape, and predominantly extends on the center region 124 of the absorption body layer 122. The liquid-absorption and distribution layer 128 protrudes over a stomach-section-side longitudinal end 130 of the center region 124 of the absorption body layer 122. It includes a mass per area of fiber material i.e., in the form of intra-cross-linked cellulose fibers (curled fiber) of for example 149 g/m² with an overall mass corresponding to the exemplary extent of about 2.8 g.

The basic layer 120, the three regions 124, 126 and 127 of the absorption body layer 122 and the body-facing liquid absorption- and distribution layer 128 have a uniform mass per area of absorption body materials across their two-dimensional extent.

The mass per area is measured as described above by analyzing a test specimen of 25 mm×25 mm, which is punched out through all previously described layers of the absorption body 7. The area 132 (25 mm×25 mm) to be punched out is always centered relative to the longitudinal center axis 44, as indicated in FIG. 8. When the mass per area in longitudinal direction 9 is determined more frontward or more rearward, the test specimen is accordingly centered relative to the longitudinal center axis 44.

It can be seen that the mass per area of absorption body material thus decreases stepwise in the direction toward a stomach-section-side end 134 and in the direction toward a back-section-side end 136 of the absorption body 7. In this way, plateaus 138 are formed between the steps. In the region of these plateaus 138, the mass per area of absorption body material of the layers of the absorption body 7 lying there underneath is preferably but not necessarily, constant.

In the shown preferred embodiment of the incontinence article, the mass per area of the absorption body 7, starting from the transverse center axis 30 anteriorly and posteriorly in the region of the overlap of the body-facing liquid absorption- and distribution layer 128 with the center region 124 of the absorption body layer 122, is essentially constant.

In FIGS. 8 and 9, plateaus 140, 141 can be seen which adjoin a step 142, 143 anteriorly or posteriorly in the longitudinal direction 9. In the region of these plateaus 140, 141, the mass per area of the absorption body 7 is significantly reduced relative to the mass per area in the region of the transverse center axis 30.

In the following, the folding of the incontinence article in pant form for the stacked arrangement of multiple incontinence articles in a packaging for distribution is described by way of the FIGS. 8, 10 and 11: as already mentioned, the transverse center axis 30 forms a first folding axis 150, about which the incontinence article is folded, so that the stomach section 4 and back section 6 can be permanently joined together for forming lateral seam regions 14 i.e., by conventional joining methods, such as gluing, ultrasound etc. Further, second folding lines 152 which approximately extend in longitudinal direction 9 are only outlined in FIG. 8, because the folding does not occur in the stretched out state shown in FIG. 8, but after finishing the pant-shaped incontinence article in the only schematically shown state in FIG. 10 *a*. Starting from this outlined state shown in FIG. 10 *a*, regions 154 of the stomach section 4 and back section 6 which laterally extend over the crotch section 8 on both sides, are folded in the direction towards the longitudinal center axis 44, preferably onto the outsides of the stomach section 4, so that the configuration outlined in FIG. 10 *b* is obtained.

Figure 10A:
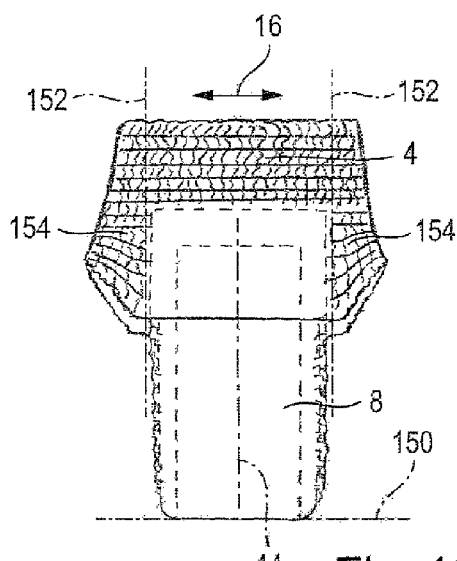
FIGS. 10 a,b,c show three schematic views of the incontinence article, illustrating the folding.
Figure 10B:
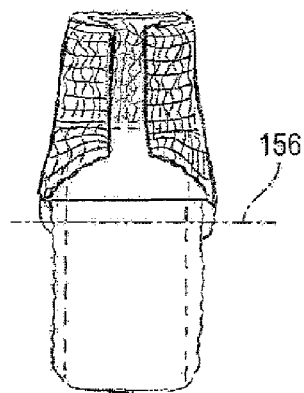
Figure 10C:
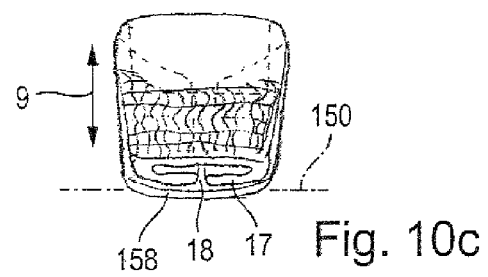

FIGS. 8 and 10 show a third folding axis 156, which extends in transverse direction 16, and whose position relative to the absorption body 7 can be seen from FIG. 8. Further folding about this only further folding axis 156, which extends in transverse direction 16, results in the compactly folded configuration of the pant-shaped incontinence article shown in FIG. 10 *c*. It can be seen that the border of the stomach and back band 17, which delimits the waist opening 18, does not protrude in longitudinal direction 9 over the outer folding edge 158 of the incontinence article, which folding edge 158 is formed by the first folding axis 150.

Figure 11:
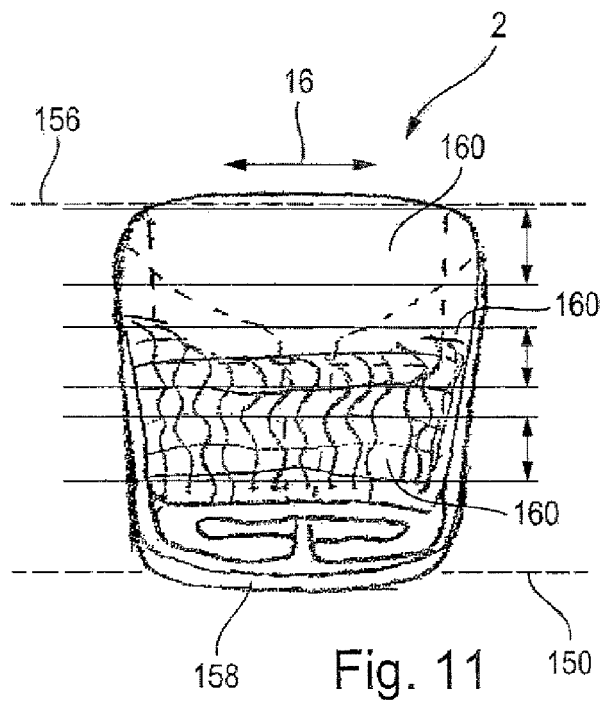
FIG. 11 shows a schematic view of the folded incontinence article, illustrating sampling during determination of the thickness.

FIG. 11 illustrates at which sites the thickness of the incontinence article 2, which is folded into the configuration of FIG. 10 *c*, is determined. As already mentioned, the entire such folded incontinence article 2 is punched out over the entire transverse direction 16 with a punching knife at a distance of about 10 mm to the folding edges or folding axes 150 and 156, thereby forming strip-shaped test specimens 160. Based on these test specimens 160, which include all layers of the incontinence article, the thickness is then determined as described above.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein.

What is claimed is:

1. An incontinence article in pant form for absorbing bodily excretions, comprising:
   a stomach section;
   a back section, spaced apart from the stomach section in a longitudinal direction of the incontinence article along a longitudinal center axis, said stomach section and back section having respective lateral seam regions and being joined at the respective lateral seam regions thereby forming a stomach- and back band which is continuous in a transverse direction of the incontinence article, and has a circumferentially closed waist opening;
   a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;
   first elastifying means extending in spaced apart and parallel relationship to one another in the transverse direction in the stomach section and back section, thereby two-dimensionally elastifying the stomach section and the back section; and
   second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacturer,
   said incontinence article having a first fold axis formed by a transverse center axis of the incontinence article,
   second fold axes respectively provided outside the absorption body on either side of the absorption body and extending in the longitudinal direction, and
   a third fold axis provided in a region of the absorption body, wherein regions of the stomach section and the back section which laterally protrude over the crotch section are folded about the second fold axes in the direction toward the longitudinal center axis, wherein after folding the incontinence article about the third folding axis, the border of the stomach and back band does not protrude over the first fold axis, i.e., not over an outer folding edge of the incontinence article formed by the first fold axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis where the absorption body has a mass per area that is at most 80% of the first mass per area, wherein the first mass per area of absorption body material decreases stepwise toward the stomach-section side end of the absorption body and/or toward a back-section side end of the absorption body, thereby forming stepped plateaus, and wherein a longitudinal extent of one of the plateaus which adjoins one of the steps in a stomach-section side portion and/or in a back-section side portion of the absorption body in longitudinal direction, and through which the third fold axis extends is at least 15% of the distance of the transverse center axis to the stomach section side end of the absorption body or to the back section side end of the absorption body.

2. The incontinence article of claim 1, wherein the mass per area of absorption body material is at least 20%, of the first mass per area.

3. The incontinence article of claim 1, wherein the plateaus are delimited by straight, step-shaped transitions extending in the transverse direction.

4. The incontinence article of claim 1, wherein the absorption body has longitudinal borders that extend straight and in longitudinal direction.

5. The incontinence article of claim 1, wherein the absorption body in has a stomach-section side half and a back-section side half, and has multiple plateaus in the stomach-section side half and/or the back-section side half, wherein a mass per area of the plateaus of absorption body material decreases from the transverse center axis along the longitudinal center axis respectively in the direction toward the stomach-section side end of the absorption body and in the direction toward the back-section site and of the absorption body, between successive ones of the plateaus.

6. The incontinence article of claim 1, wherein the absorption body has as a first basic layer and an absorption body layer arranged above the first basic layer, said absorption body layer varying in its mass per area over its extend, thereby resulting in a three-dimensional topology over an extent of the absorption body layer, said absorption body preferably having a in particular hourglass-shaped, body-facing liquid-absorption and distribution layer arranged on the absorption body layer.

7. The incontinence article of claim 1, wherein the first mass per area of the absorption body remains essentially constant over an extent of at least 20%, of a distance of the transverse center axis to the stomach-section side end of the absorption body or to the back-section-side end of the absorption body.

8. The incontinence article of claim 1, wherein the third fold axis extends in one or both of the respective overlapping regions.

9. An incontinence article in pant form for absorbing bodily excretions, comprising:
   a stomach section;
   a back section, spaced apart from the stomach section in a longitudinal direction of the incontinence article along a longitudinal center axis, said stomach section and back section having respective lateral seam regions and being joined at the respective lateral seam regions thereby forming a stomach- and back band which is continuous in a transverse direction of the incontinence article, and has a circumferentially closed waist opening;
   a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;
   first elastifying, means extending in spaced apart and parallel relationship to one another in the transverse direction in the stomach section and back section, thereby two-dimensionally elastifying the stomach section and the back section; and
   second elastifyinq means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacturer,
   said incontinence article having a first fold axis formed by a transverse center axis of the incontinence article,
   second fold axes respectively provided outside the absorption body on either side of the absorption body and extending in the longitudinal direction, and
   a third fold axis provided in a region of the absorption body, wherein regions of the stomach section and the back section which laterally protrude over the crotch section are folded about the second fold axes in the direction toward the longitudinal center axis, wherein after folding the incontinence article about the third folding axis, the border of the stomach and back band does not protrude over the first fold axis, i.e., not over an outer folding edge of the incontinence article formed by the first fold axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis where the absorption body has a mass per area that is at most 80% of the first mass per area, wherein a thickness of the folded incontinence article measured under a test pressure of 20 g/cm$^2$ at three different sites, a first site spaced apart by 10 mm from a border associated with the first fold axis, a second site spaced apart by 10 mm from a border associated with the third fold axis, and a third site located between the first site and the second site, deviates by less than 6% from an arithmetic mean value of the measurements taken at the three sites.

10. The incontinence article of claim 9, wherein the mass per area of absorption body material is at least 20% of the first mass per area.

11. The incontinence article of claim 9, wherein the absorption body has a stomach-section side half and a back-section side half, and has multiple plateaus in the stomach-section side half and/or the back-section side half, wherein a mass per area of the plateaus of absorption body material decreases from the transverse center axis along the longitudinal center axis respectively in the direction toward the stomach-section side end of the absorption body and in the direction toward the back-section site and of the absorption body, between successive ones of the plateaus.

12. The incontinence article of claim 9, wherein the absorption body as a first basic layer and an absorption body layer arranged above the first basic layer, said absorption body layer varying in its mass per area over its extend, thereby resulting in a three-dimensional topology over an extent of the absorption body layer, said absorption body having an hourglass-shaped, body-facing liquid-absorption and distribution layer arranged on the absorption body layer.

13. The incontinence article of claim 9, wherein the first mass per area of the absorption body remains essentially constant over an extent of at least 20% of a distance of the transverse center axis to, the stomach-section side end of the absorption body or to the back-section-side end of the absorption body.

14. An incontinence article in pant form for absorbing bodily excretions, comprising:
   a stomach section;
   a back section, spaced apart from the stomach section in a longitudinal direction of the incontinence article along a longitudinal center axis, said stomach section and back section having respective lateral seam regions and being joined at the respective lateral seam regions thereby forming a stomach- and back band which is continuous in a transverse direction of the incontinence article, and has a circumferentially closed waist opening;
   a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;

first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacturer, said incontinence article having a first fold axis formed by a transverse center axis of the incontinence article, second fold axes respectively provided outside the absorption body on either side of the absorption body and extending in the longitudinal direction, and a third fold axis provided in a region of the absorption body, wherein regions of the stomach section and the back section which laterally protrude over the crotch section are folded about the second fold axes in the direction toward the longitudinal center axis, wherein after folding the incontinence article about the third folding axis, the border of the stomach and back band does not protrude over the first fold axis, i.e., not over an outer folding edge of the incontinence article formed by the first fold axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis where the absorption body has a mass per area that is at most 80% of the first mass per area, wherein an extent of the respective lateral seams in the longitudinal direction is 100-170 mm, wherein a ratio between the extent of the respective lateral seems longitudinal direction and the extent of the incontinence article between the border of the stomach- and back sections and the transverse center axis is at most 0.42.

15. An incontinence article in pant form for absorbing bodily excretions, comprising:

a stomach section;

a back section, spaced apart from the stomach section in a longitudinal direction of the incontinence article along a longitudinal center axis, said stomach section and back section having respective lateral seam regions and being joined at the respective lateral seam regions thereby forming a stomach- and back band which is continuous in a transverse direction of the incontinence article, and has a circumferentially closed waist opening;

a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;

first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacturer, said incontinence article having a first fold axis formed by a transverse center axis of the incontinence article, second fold axes respectively provided outside the absorption body on either side of the absorption body and extending in the longitudinal direction, and a third fold axis provided in a region of the absorption body, wherein regions of the stomach section and the back section which laterally protrude over the crotch section are folded about the second fold axes in the direction toward the longitudinal center axis, wherein after folding the incontinence article about the third folding axis, the border of the stomach and back band does not protrude over the first fold axis, i.e., not over an outer folding edge of the incontinence article formed by the first fold axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis where the absorption body has a mass per area that is at most 80% of the first mass per area, wherein in the stomach section and/or in the back section the ratio between a distance of the first elastifying means in longitudinal direction to each other and a distance of an outermost waist-facing one of the first elastifying means to an innermost crotch-facing one of the first elastifying means is between 0.08 and 0.25.

16. The incontinence article of claim 15, wherein in the stomach section and in the back section a ratio between a distance of an outermost waist-facing one of the elastifying means in longitudinal direction to an innermost crotch—facing one of the first elastifying means and the extent of the incontinence article between the border of the stomach- and back and the transverse center axis is at most 0.3.

17. An incontinence article in pant form for absorbing bodily excretions, comprising:

a stomach section;

a back section, spaced apart from the stomach section in a longitudinal direction of the incontinence article along a longitudinal center axis, said stomach section and back section having respective lateral seam regions and being joined at the respective lateral seam regions thereby forming a stomach- and back band which is continuous in a transverse direction of the incontinence article, and has a circumferentially closed waist opening;

a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;

first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the article is brought into folded configuration by the manufacturer, said incontinence article having a first fold axis formed by a transverse center axis of the incontinence article, second fold axes respectively provided outside the absorption body on either side of the absorption body and extending in the longitudinal direction, and a third fold axis provided in a region of the absorption body, wherein regions of the stomach section and the back section which laterally protrude over the crotch section are folded about the second fold axes in the direction toward the longitudinal center axis, wherein after folding the incontinence article about the third folding axis, the border of the stomach and back band does not protrude over the first fold axis, i.e., not over an outer folding edge of the incontinence article formed by the first fold axis, wherein a mass per area of the absorption body decreases from a first mass per area in a region of the transverse center axis, respectively toward a stomach-section side end of the absorption body and toward a back-section side end of the absorption body, and wherein the third fold axis is arranged at a distance to the transverse center axis where the absorption body has a mass per area that is at most 80% of the first mass per area, wherein the first elastifying means are fixed with a pre-tension which is greater by at least 1.1 than a pre-tension with which the second elastifying means are fixed.

18. The incontinence article of claim 17, wherein a thread strength of the first elastifying means is at least 1000 dtex and/or wherein the thread strength of the second elastifying means is 500-1100 dtex.

* * * * *